United States Patent [19]

Jacobs et al.

[11] Patent Number: 4,950,812

[45] Date of Patent: Aug. 21, 1990

[54] SINGLE-STEP CATALYTIC PROCESS FOR THE DIRECT CONVERSION OF POLYSACCHARIDES TO POLYHYDRIC ALCOHOLS

[75] Inventors: Pierre Jacobs, Gooik; Herve Hinnekens, Gent, both of Belgium

[73] Assignee: Fina Research S.A., Belgium

[21] Appl. No.: 313,946

[22] Filed: Feb. 22, 1989

[30] Foreign Application Priority Data

Feb. 22, 1988 [EP] European Pat. Off. .......... 88870023

[51] Int. Cl.$^5$ .................. C07C 29/132; C07C 29/14; C07C 31/18; C07C 31/26
[52] U.S. Cl. .................... 568/863; 502/244; 502/259; 502/260; 502/261; 502/325; 502/337; 502/345
[58] Field of Search ........................................ 568/863

[56] References Cited

U.S. PATENT DOCUMENTS

| | | | |
|---|---|---|---|
| 2,609,399 | 9/1952 | Kool et al. | 568/863 |
| 3,963,788 | 6/1976 | Kruse et al. | 568/863 |
| 3,963,789 | 6/1976 | Kruse et al. | 568/863 |

OTHER PUBLICATIONS

608A, Bull. Ste chimique de France (1981) juillet-aout, Partie II, Paris, France, with translation thereof.
Chemical Abstracts 72, 134408 (1970), p. 109.

Primary Examiner—J. E. Evans
Attorney, Agent, or Firm—Arnold, White & Durkee

[57] ABSTRACT

A single-step process for the conversion of polysaccharides to polyhydric alcohols by hydrogenation at high pressure and temperature in the presence of a catalyst comprising (i) a supported metal selected from ruthenium, copper, nickel, cobalt and their mixtures, the metal being highly dispersed on the support so as to be capable of adsorbing more than 0.58 molecules of CO per atom of metal, and (ii) a solid having acidic functions, which may or may not be identical to the support, the solid having sufficient acid functions so that the rate constant of hydrolysis of sucrose on the catalyst is greater than 70% of the rate constant of hydrogenation of glucose on the catalyst. The process gives substantially pure polyhydric alcohols in a single step.

23 Claims, No Drawings

SINGLE-STEP CATALYTIC PROCESS FOR THE DIRECT CONVERSION OF POLYSACCHARIDES TO POLYHYDRIC ALCOHOLS

BACKGROUND OF THE INVENTION

The invention relates to the production of substantially pure polyhydric alcohols. More particularly, this invention relates to a single-step process for the catalytic production of substantially pure polyhydric alcohols from polysaccharides. A particular mode of the invention relates to the simultaneous hydrolysis and hydrogenation of polysaccharides, using an heterogeneous catalyst, to produce substantially pure hexitols.

The term "carbohydrate" as used herein includes monosaccharides, polysaccharides, and mixtures of monosaccharides and/or polysaccharides.

The term "polysaccharide" as used herein includes those saccharides containing more than one monosaccharide unit. This term thus includes disaccharides and oligosaccharides.

The supported nickel catalysts supported on carbon, diatomaceous earth or kieselguhr, as described in U.S. Pats. No. 3,538,019 and 3,670,035 (which is a division of U.S. Pat. No. 3,538,019) have high activity for the conversion of both monosaccharides and polysaccharides, including carbohydrate mixtures such as corn starch hydrolzate, with high selectivity to sorbitol when either corn starch hydrolyzate or dextrose is used as the starting material. A disadvantage of the catalysts described in U.S. Pats. No. 3,538,019 and 3,670,035 is that they cannot be regenerated; when reactivation is required, it is necessary to remove the active catalyst material from the support by chemical means and then to redeposit the catalyst metal on the support. Various other nickel catalysts for conversion of carbohydrates to polyhydric alcohols are cited in U.S. Pats. No. 3,538,019 and 3,670,035.

The conversion of carbohydrates to polyhydric alcohols using ruthenium on a solid carrier is known. U.S. Pat. No. 2,868,847 discloses the use of ruthenium on an inert catalyst support such as carbon, alumina, silica, or kieselguhr, as a catalyst for the catalytic hydrogenation of mono- and disaccharides, the latter being hydrolyzed and hydrogenated to hexitols. However, maltose, a disaccharide containing two glucose units, was more easily converted to maltitol, a $C_{12}$ alcohol, according to the patent.

The hydrogenation of aqueous solutions of carbohydrates over zerovalent group VIII metals dispersed on alpha-alumina is disclosed in U.S. Pat. No. 4,380,680.

The hydrogenation of monosaccharides using a supported ruthenium, palladium, platinum, or nickel catalyst (activated carbon was used as the support in all experimental work) is discussed in an article by N. A. Vasyunina et al. "Catalytic Properties of Ruthenium in Monosaccharides Hydrogenation Reaction" in Izvestiya Akademii Nauk SSR Khimicheskaya Serya 4:848.854 (1969). Ruthenium was found to have higher activity than the other three catalysts.

A two stage process for hydrogenation of ligneous and other plant material such as wood sawdust is disclosed in Izv. Akad. Nauk SSR. Otd. Khim. 8:1522.1523 (1960). The process consists of a first stage hydrolytic hydrogenation of polysaccharides in an acid medium, followed by a second stage hydrogenation of the lignin in an alkaline medium using a ruthenium catalyst in both stages. In a specific embodiment, pine sawdust is treated using an aqueous phosphoric acid medium and a ruthenium-on-carbon catalyst. The first stage reaction product is filtered to separate the liquid medium from the crystals obtained from the first stage filtrate.

Belgian Patent No. 837,201 and U.S. Pats. No. 3,963,788, 3,963,789 and 4,072,628 disclose a two-stage high-pressure process for the conversion of carbohydrates to polyhydric alcohols in the presence of a ruthenium-containing catalyst prepared by depositing $RuCl_3$ on a support which is either a zeolite catalyst having a Si/Al molar ratio greater than 3, or a clay. The catalyst can be regenerated by contacting it with an aqueous solution of a mineral acid.

A process for the continuous preparation of polyhydric alcohols over lumps of catalyst, made of ruthenium supported on animal coal, was disclosed in U.S. Pat. No. 4,520,211. However, a series of two consecutive reactors was necessary. Further, it was necessary to lower the pH of the aqueous carbohydrate solution to about 2.5 to 4.5.

However, the known procedures have serious disadvantages. First of all, the catalysts used therein cannot be regenerated. Also, they do not allow the preparation of polyhydric alcohols directly from polysaccharides and they must therefore use expensive pure monosaccharides instead of the less expensive polysaccharides.

Thus, although various catalytic processes for the conversion of carbohydrates to polyhydric alcohols are known in the art, none of them shows all desirable features, e.g. a single-step process combining hydrolysis and hydrogenation, substantial purity of the products, and no requirement for prior activation of the feedstocks. There is accordingly a need in the art for an improved process which would possess all these characteristics.

BRIEF SUMMARY OF THE INVENTION

An object of the invention is to provide a process for the production of substantially pure polyhydric alcohols.

A further object of the invention is to provide a catalytic process for the conversion of polysaccharides to polyhydric alcohols, wherein the catalyst may be regenerated.

Still another object of the invention is to provide a process for the production of polyhydric alcohols in one step directly from water-insoluble polysaccharides.

The present invention is a single-step process for the production of a polyhydric alcohol from a polysaccharide by contacting said polysaccharide in an aqueous medium with hydrogen at elevated temperature and pressure in the presence of a catalyst comprising or consisting of (i) a supported metal selected from ruthenium, copper, nickel, cobalt and mixtures thereof, and (ii) a solid having acidic functions, which solid may or may not be identical to the support, wherein (a) the metal is highly dispersed on the support to be capable of adsorbing more than 0.58 molecules of CO per atom of metal, and (b) the solid has sufficient acid functions so that the rate constant of hydrolysis of sucrose on the catalyst is greater than 70% of the rate constant of hydrogenation of glucose on the catalyst.

DETAILED DESCRIPTION

Conversion of polysaccharides to polyhydric alcohols involves hydrolysis of the polysaccharide and hydrogenation of the monosaccharide thus produced.

Known processes have heretofore been limited to starting materials which are readily hydrolysable to monosaccharides. These previously known processes have further been limited to multi-step operation, wherein the hydrolysis and the hydrogenation are to be carried out in different steps.

In contrast with the prior art, the present process is a single-step process, which may also be used to produce polyhydric alcohols from high molecular weight polysaccharides such a cellulose and insoluble starch.

The process of the invention represents a significant improvement over known prior art such as U.S. Pats. No. 3,963,788, 3,963,789, 4,072,628 and 4.520,211 and Belgian Patent No. 837,201, since it is the first effective procedure which permits the one-step conversion of natural feedstocks in a reduced reaction time in the same conditions of conversion of monosaccharides.

Another advantage of the invention is that the occurrence of by-products and the degradation of the catalyst are both negligible under the reaction conditions used. Further, no purification is required, whether before the reaction or after the reaction (except for the removal of the catalytic material, e.g. by a simple filtration).

The importance of the process of the invention lies in the fact that polyhydric alcohols such as D-glucitol and D-mannitol can be obtained easily and with high purity from cheap starting materials such as starch.

Polysaccharides are hydrolyzed to their basic monosaccharide or monosaccharides, whose aldehyde or ketone groups are then hydrogenated to hydroxyl groups to produce the corresponding polyhydric alcohol or alcohols. The nature of the products is known in the art and need not be further described.

The catalyst is prepared by depositing a metal selected from the group consisting of ruthenium, copper, nickel, cobalt, and mixtures thereof, in finely divided form onto a suitable carrier material, using conventional means.

Applicants have found that in order to achieve the objects of the invention, it is essential that the metal present on the support be highly dispersed to be capable of adsorbing more than 0.58 molecules of CO per atom of metal.

Chemisorption measurements are conventional in the art to evaluate the dispersion of metals on supported metal catalysts. CO chemisorption on supported metal catalysts, as herein construed, is measured by a flow method in a modified gas chromatograph provided with a thermal conductivity detector. The injector and detector temperatures are maintained at 523° K. The catalyst is contained in a metal microreactor of approximately 5 mm inner diameter and 30 mm length, which replaces the original column. The catalyst is held in place by means of quartz wool. Prior to a chemisorption measurement, the sample is first flushed with helium at room temperature for 10 min. The gas is changed to hydrogen, first at room temperature during 10 min., then at a temperature increasing from 298° K. to 423° K. at a rate of 6° K. min. and maintained at 423° K for 14 minutes. Finally, the catalyst is treated in flowing helium at 423° K. for 3 hours and the sample is then cooled to room temperature. Chemisorption measurements are made by injecting 1 ml pulses of 3% CO in He through 0.4 ml of catalyst sample at 298° K. until CO is fully eluted. The volume of adsorbed gas is obtained by measuring the difference between the areas of the eluted and injected pulses.

The flow rate used throughout the sample conditioning and the chemisorption determinations is 27 ml./min./l.

Among the various known techniques for preparing supported metal catalysts are impregnation, ion exchange or vapor deposition. Applicants have found that ion exchange with amine complex salts permits product of highly dispersed supported metals, to be capable of adsorbing more than 0.58 molecule of CO per atom of metal.

It has been observed that the preparation method influences the catalytic properties, and that said properties are best evidenced by chemisorption measurements.

As known in the art, the supported metal catalyst is obtained from the ion exchanged material by successively washing said material, drying it, and heating it under a flow of hydrogen at a temperature slowly increasing up to from 423 to 773° K., preferably not above 623° K. During this activation procedure, the amine complex salt is decomposed, and the metallic ions are reduced to the metal state. Once activated, the supported metal catalyst may be exposed to air without any loss of properties.

The second component of the catalyst used in the process of the invention is a solid having sufficient acid functions so that the rate constant k1 of hydrolysis of sucrose on the catalyst is greater than 70% of the rate constant of hydrogenation k2 of glucose on the catalyst.

The rate constant k1 of hydrolysis of sucrose, as herein construed, is determined in aqueous solution, at a temperature of 423° K., under a pressure of 1.79 MPa, under such conditions that the initial weight ratio of sucrose to acid solid is about 50 when the sucrose concentration equals 30% of its initial value.

The rate constant k2 of hydrogenation of glucose, as herein construed, is determined in aqueous solution, at a temperature of 423° K., under a pressure of 1.79 MPa, under such conditions that the initial weight ratio of D-glucose to metal is about 1000 when the D-glucose concentration equals 30% of its initial value.

Preferably, the rate constant k1 of hydrolysis of sucrose on the catalyst should be greater than about 0.006 s 1.

If the support is different, there may be used as the support suitable carried materials which have no adverse effect on the hydrolysis reaction nor on the hydrogenation reaction, such as active carbon, aluminum oxide, titanium dioxide, kieselguhr, silica gel, zeolites, and molecular sieves, with active carbon being preferred. The weight ratio between the two components of the catalyst is not a very important parameter, as long as the ratio k1 : k2 is greater than 7:10. It is preferred to use approximately equal weights of supported metal and of solid having acid functions. The rate constants k1 and k2 may be determined on the separate components, provided that the ratio k1/k2 is corrected for the weight ratio of the components. If the support is the solid having acidic functions, the solid having acidic functions may be selected from silica-alumina, silica-magnesia, silica-titania and acidic zeolites of natural or synthetic origin.

Zeolites are ordinarily synthesized in the sodium form and other metallic ions or ammonium can be introduced into the zeolite by ion exchange, as is well known in the art. Zeolites in the hydrogen form can be obtained by decomposition of the ammonium form at high temperature, according to methods known in the art. The structure of zeolites is discussed extensively in D.

L. Breck "Zeolite Molecular Sieves," published by John Wiley and Sons, New York, 1974. A comprehensive review of zeolite catalysts is contained in an article by J. Turkevitch, Catalysis Reviews, 1, 1.35 (1967).

The zeolites are crystalline aluminosilicates in which the aluminum, silicon and oxygen atoms are arranged in a rigid, dimensional network having interval cavities of molecular size and pores of uniform size which provide access to these cavities. The crystal network includes $SiO_4$ and $AlO_4$ tetrahedra; the negative charge on the latter is balanced by cations (e.g., metal ions, ammonium ions, or hydrogen ions). The crystal structure of zeolites has been discussed extensively in the literature and will not be discussed at length here.

Whenever a zeolite is used as the support, it should have intermediate pore sizes and a three-dimensional network of channels for obtaining a high metal dispersion thereon. One category of zeolites having said properties is the faujasite-type zeolites, which are preferred as supports having acid functions. Faujasite type zeolites are characterized by a silica/alumina molar ratio of at least about 3, and effective pore size of at least about 8 $\mu$m in the hydrogen form, and a three-dimensional network of channels. Examples of catalysts of this type are Ultrastable Faujasite Y (hydrogen form), commercially available from W. R. Grace and Co.; zeolite LZY-52 form available from Linde Division of Union Carbide Corporation; zeolite ZSM-3 described by Kokotailo and Ciric in Advances in Chemistry Series 101 (1971) p. 108, and ZSM-20 disclosed in U.S. Pat. No. 3,972,983.

Many other zeolites in the hydrogen form may be used as solids having acidic functions, such as HZSM-5, H-Beta or H Mordenite. They do not present the characteristics which would allow a high metal dispersion thereon, and they may thus not be used as suitable carriers for the deposited metal.

As suitable polysaccharide starting material for the process of the invention, there may be cited the disaccharides such as sucrose, maltose, lactose and cellobiose, the oligosaccharides such as raffinose, and the polysaccharides such as insuline or starch, preferably corn starch or degradation products of starch or cellulose.

The present process uses an aqueous reaction medium. The initial polysaccharide concentration is usually about 10 to 80 wt%, preferably about 25 to 60 wt %. Suspensions may also be used when the starting material is not readily soluble.

The amount of catalyst to be used in the process of the invention may vary over a wide range and will depend upon the particular catalyst, carbohydrate, temperature and pressure which are employed in the process. In general, catalyst concentrations range from 0.04 to 8.0 wt % of metal based on the initial weight of polysaccharide, preferably from 0.04 to 2.0 wt % when ruthenium is selected, or from 0.2 to 8.0 wt % when copper, nickel or cobalt is selected. When ruthenium is used, the catalyst concentration should most preferably be of from 0.04 to 0.12 wt % for disaccharides and from 0.08 to 0.3 wt % for higher polysaccharides.

The temperature and pressure used in the process of the invention may vary over wide ranges. The process may be carried out at temperatures from 348 to 523° K., preferably from 373 to 443° K. for disaccharides and from 428 to 483° K. for polysaccharides. The hydrogen pressure should be in excess of about 1 MPa to ensure adequate contact with the carbohydrate and to achieve rapid hydrogenation.

The time of reaction will depend upon the specific starting material concentration, the specific catalyst used, pressure and temperature. Usually, the duration of reaction is about 30 to 180 minutes. Some reactions are to be continued for longer periods of time to ensure complete hydrolysis and hydrogenation, in which case it is preferable to carry out the process at a temperature not exceeding about 433° K.

The reactants may be added to the reaction chamber in any suitable manner or in any suitable order. It is preferred to add the catalyst to the aqueous solution or suspension of the carbohydrate and then add the hydrogen under pressure and commence heating the mixture to the desired temperature.

The reaction is carried out in any suitable type of apparatus which enables intimate contact of the reactants and control of the operating conditions and which is resistant to the high pressures involved. The process may be carried out in batch, semi-continuous, or continuous operation. Batch operation in a conventional autoclave gives excellent results.

Upon completion of the reaction, the catalyst is removed by centrifugation, filtration or decantation, and the polyhydric alcohol may be separated from the filtrate by any suitable means, such as crystallization, solvent extraction or evaporation.

The catalysts used in the process of the invention are highly resistant to deactivation, thereby allowing prolonged use of said catalyst without reactivation. It has been found that the catalyst used in the process of the invention may be used for the one-step batch conversion of starch in up to about ten consecutive hydrogenation runs before reactivation is required. For disaccharides this reactivation can be conducted even less frequently. Reactivation is conducted in a similar manner to activation. Thus the catalysts are washed till carbohydrate-free, dried at room temperature, and heated under a flow of hydrogen at a temperature slowly increasing to a value of from 423 to 773° K., preferably not above 623° K.

The invention will now be described further by way of the following examples.

Examples 1 to 5

(a) Preparation of Ru on acid ultrastable Y Zeolite (HUSY).

Zeolite NaY LZY-52 powder was obtained from Union Carbide Corporation.

Ultrastabilization of zeolite NaY was achieved as follows. It was first exchanged with a 0.1 M aqueous solution of $NH_4Cl$ in a 100-fold excess with respect to the cation exchange capacity (CEC). The $(NH_4-Na)Y$ zeolite thus obtained was washed till Cl-free and found to be exchanged for 70% of the CEC. This material was then dried at 320° K. and equilibrated in an atmosphere of 80% humidity (over a saturated $NH_4Cl$ aqueous solution).

This sample was calcinated for 12 hours in a furnace preheated at 723° K. This calcined $(NH_4-Na)Y$ sample was then exchanged again with $NH_4+$ ions, dried, equilibrated in moisture and calcined a second time in a furnace preheated at 1073° K. After a third $NH_4+$ exchange a sodium-free material is obtained which is denoted as HUSY.

Ru-zeolite was prepared by ion exchange with $Ru_3+$ hexamine. The ion exchange was carried out with 593.6 ml of a 0.05 M aqueous solution of $Ru(NH_3)_6Cl_3$ for 10 g of HUSY.

The ion exchanged materials were washed till chloride free and dried at room temperature. Activation of the catalyst was performed by heating it at about 2 K/min. to about 673° K., under a flow of hydrogen. Thus the Ru-amine complex was decomposed and the Ru (III) reduced to the metal state. The catalyst contained 3% Ru with a Ru dispersion of 0.73 as measured by the molar ratio of adsorbed CO on Ru (according to the above-described method). The ratio k1/k2 (as above defined) was 0.91.

(b) Simultaneous hydrolysis and hydrogenation of corn starch.

150 ml of an aqueous suspension of corn starch was loaded in a 600 ml Parr autoclave, and the catalyst, prepared as above described, was added. After closing and purging the autoclave, it was heated under hydrogen pressure while stirring the mixture at 1000 rpm. After the necessary reaction time to complete the hydrogenation given in Table I, the reactor was cooled, the reaction mixture was filtered to remove the catalyst, and the filtrate was analyzed by gas-liquid chromatography. For high pressure liquid chromatography the filtrate was injected as such. For gas-liquid chromatography the samples were silanated with trimethylsilane. The separation of the trimethylsilyl ethers was done from 300° K. to 478° K. using a temperature programming of 3° K./min. The column was a 3 m packed column with 3% OV-225 on Gaschrom Q. As internal standard the trimethylsilyl derivative of phenyl-beta-D-glucopyranos was used. In liquid chromatography the "carbohydrate" column purchased from Chrompack was used, with water as solvent at a pressure of 7.2 MPa. In this case a calibration curve was determined for each component.

The operating conditions and the product composition are given in Table I.

TABLE I

| Example No. | 1 | 2 | 3 | 4 | 5 |
| --- | --- | --- | --- | --- | --- |
| Operating conditions | | | | | |
| Starch concentration (%) | 25 | 10 | 10 | 50 | 30 |
| Re/Starch (g/g) | 0.0018 | 0.0036 | 0.0012 | 0.0020 | 0.0018 |
| Temperature (°K.) | 453 | 453 | 403 | 453 | 453 |
| $H_2$ pressure (MPa) | 5.52 | 5.52 | 5.52 | 5.52 | 5.52 |
| Duration (h) | 0.58 | 0.6 | 41 | 1 | 1 |
| Product composition (%) | | | | | |
| Total alditols | 99 | 99.9 | 100 | 99.8 | 97 |
| Total hexitols | 97 | 92 | 96.5 | 97.8 | 94 |
| D-glucitol | 96 | 87 | 95.0 | 92 | 92 |
| D-mannitol | 1 | 5 | 1.5 | 5.8 | 2 |
| Xylitol | 2 | 7.9 | 3.5 | 2 | 3 |

The sum of total hexitols and xylitol necessarily equals the total amount of alditols, since the products are expressed in mole %. When the total alditol percentage does not equal 100%, it indicates the presence of traces of D-glucose.

In Example 4, the catalyst used was the catalyst recovered by filtration in Example 2. In Example 5, the catalyst had been used for 17 successive batch processes. These examples show that the process of the invention may be performed many times before the catalyst eventually requires a regeneration step. The exact amounts of D-glucitol, D-mannitol and xylitol depend mainly on the operating conditions. Xylitol is formed by hydrogenolysis of hexitols on the Ru metal. Isomerisation of D-glucitol into D-mannitol is sometimes observed depending upon the operating conditions but its isomerization into L-iditol was not observed.

COMPARATIVE EXAMPLE 1.

The procedure of Example 1 was repeated with the exceptions (i) that the concentration of starch was 30%, and (ii) that the Ru on ultrastable zeolite catalyst was made as described in Belgian Patent No. 837,201 (CO/Ru=0.49). After 1 hour of reaction, less than 20% alditols were obtained.

EXAMPLES 6 and 7

Aqueous solutions of (+)- sucrose (Example 6) and (+)- lactose (Example 7) were loaded in a Parr autoclave where they were simultaneously hydrolysed and hydrogenated in the presence of a Ru-zeolite catalyst prepared as above described.

The operating conditions and the product composition are given in Table II.

TABLE II

| Example No. | 6 | 7 |
| --- | --- | --- |
| Operating conditions | | |
| Disaccharide | (+)-sucrose | (+)-lactose |
| Concentration (%) | 40 | 30 |
| Ru/Starch (g/g) | 0.0006 | 0.0009 |
| Temperature (°K.) | 403 | 433 |
| $H_2$ pressure (MPa) | 5.52 | 5.52 |
| Duration (h) | 0.8 | 0.38 |
| Product composition (%) | | |
| D-glucitol | 72 | 50 |
| D-mannitol | 28 | ? |
| Xylitol | — | 50 |

These examples confirm that the process of the invention, although particularly adapted to the one-step conversion of higher polysaccharides, such as starch, may also be used for disaccharides.

EXAMPLE 8

A 5% Ru/HUSY catalyst was prepared according to the procedure described in Example 1(a) by using 989.4 ml of an aqueous 0.005M solution of $Ru(NH_3)_6 Cl_3$ for 10 g of HUSY.

A 30% aqueous solution of corn starch was loaded with the catalyst (with a Ru:starch weight ratio of 0.0018) in an autoclave and stirred at 1000 rpm. After 0.8 hour of reaction at a temperature of 453° K. under an hydrogen pressure of 5.52 MPa, 99.5% of alditols were formed, of which 97% were D-glucitol and 2.5% xylitol.

EXAMPLES 9 to 13

(a) Preparation of the dual-component catalyst.

Ruthenium deposited on carbon in an amount of 5 wt % is available commercially from Johnson Matthey Chemicals.

The rate constant k2 of hydrogenation of glucose on this 5% Ru/C material was determined to be 0.0083 s 1 (under the above-described conditions).

The 5% Ru/C component was mixed in a 1:1 weight ratio with the following acidic zeolites:

Examples 9 to 11 : HUSY prepared as in Example 1(a).

Example 12 : H-Mordenite (obtained from Norton Co.).

Example 13 : HZSM-5. prepared from ZSM-5 (U.S. Pat. No. 3,702,886) by calcination at a temperature of 673° K. for 24 hours, exchange in a boiling 0.5 N HCl aqueous solution for 0.5 hour, washing till chloride free and drying at 373° K.

The rate constants k1 of hydrolysis of sucrose (as above defined) for these materials are stated in Table III.

(b) Simultaneous hydrolysis and hydrogenation of polysaccharides.

Aqueous solutions of polysaccharides were loaded with the catalyst in an autoclave and stirred at 1000 rpm.

The operating conditions and the product composition are stated in Table III.

TABLE III

| Example No. | 9 | 10 | 11 | 12 | 13 |
|---|---|---|---|---|---|
| Acidic zeolite | HUSY | HUSY | HUSY | H-Morden. | HZSM-5 |
| $k_1$ ($s^{-1}$) | 0.00752 | 0.00752 | 0.00752 | 0.00833 | 0.0141 |
| Operating conditions | | | | | |
| Polysaccharide | Corn Starch | (+) sucrose | (+) lactose | Corn Starch | Corn Starch |
| $k_1/k_2$ | 0.91 | 0.91 | 0.91 | 1.00 | 1.70 |
| concentration (%) | 30 | 30 | 30 | 30 | 30 |
| Ru/polysaccharide (g/g) | 0.003 | 0.0005 | 0.0002 | 0.003 | 0.003 |
| Temperature (°K.) | 453 | 423 | 453 | 453 | 453 |
| H$_2$ pressure (MPa) | 1.79 | 1.79 | 1.79 | 1.79 | 1.79 |
| Duration (h) | 1.5 | 0.75 | 1.5 | 2.0 | 1.0 |
| Product composition (%) | | | | | |
| Total alditols | 100 | 100 | 100 | 100 | 100 |
| Total hexitols | 95 | 100 | 99.3 | 99.6 | 97.7 |
| Total pentitols | 5 | 0 | 0.7 | 0.4 | 2.3 |

What is claimed is:

1. A single-step process for the production of polyhydric alcohol from a polysaccharide comprising contacting said polysaccharide in an aqueous medium with hydrogen at elevated temperature and pressure in the presence of a catalyst which comprises: (i) a supported metal selected from the group consisting of ruthenium, copper, nickel, cobalt and mixtures thereof, and (ii) a solid having acidic functions, wherein (a) the metal is highly dispersed on the support to be capable of absorbing more than 0.58 molecules of CO per atom of metal, and (b) the solid has sufficient acid functions so that the rate constant of hydrolysis of sucrose on the catalyst is greater than 70% of the rate constant of hydrogenation of glucose on the catalyst.

2. The process of claim 1 wherein the supported metal is prepared by ion exchange.

3. The process of claim 1, wherein the supported metal is prepared using an amine complex salt which is then decomposed.

4. The process of claim 1, wherein the supported metal is ruthenium.

5. The process of claim 1, wherein the support is selected from the group consisting of silica-alumina, silica-magnesia, silica-titania, acidic zeolites of natural or synthetic origin, active carbon, aluminum oxide, titanium oxide, kieselguhr, silica gel, and molecular sieves.

6. The process of claim 1, wherein the support is identical to the solid having acidic functions, said solid being a synthetic acidic zeolite having intermediate pore sizes and a three-dimensional network of channels.

7. The process of claim 1, wherein the solid is acid ultrastable zeolite Y.

8. The process of claim 1, wherein the support is different from the solid having acidic functions, said support being active carbon.

9. The process of claim 1, wherein the initial polysaccharide concentration is of from 10 to 80 wt %.

10. The process of claim 1, wherein the initial polysaccharide concentration is from 25 to 60 wt %.

11. The process of claim 1, wherein the catalyst concentration is from 0.04 to 8.0 wt % of metal, based on the initial weight of polysaccharide.

12. The process of claim 1, wherein the temperature is from 348 to 523° K.

13. The process of claim 1, wherein the hydrogen pressure is in excess of about 1 MPa.

14. The process of claim 1, wherein the reaction time is from 30 to 180 minutes.

15. The process of claim 1, wherein the reaction time more than 180 minutes and the temperature does not exceed about 433° K.

16. The process of claim 1, wherein the polysaccharide is a disaccharide.

17. The process of claim 1, wherein the temperature is from 373 to 443° K.

18. The process of claim 1, wherein the catalyst concentration is from 0.04 to 0.12 wt % of metal, based on the initial weight of disaccharide.

19. The process of claim 1, wherein the polysaccharide is formed of more than two monosaccharide units.

20. The process of claim 1, wherein the polysaccharide is starch.

21. The process of claim 18, wherein the catalyst concentration is from 0.08 to 0.3 wt % of metal, based on the initial weight of polysaccharide.

22. The process of claim 19, wherein the catalyst concentration is from 0.08 to 0.3 wt % of metal, based on the initial weight of polysaccharide.

23. The process of claim 1, wherein the support and the acidic functions have the same composition.

* * * * *